Jan. 15, 1974 C. H. FISCHER Plant Pat. 3,442
GLADIOLUS PLANT
Filed Nov. 15, 1971
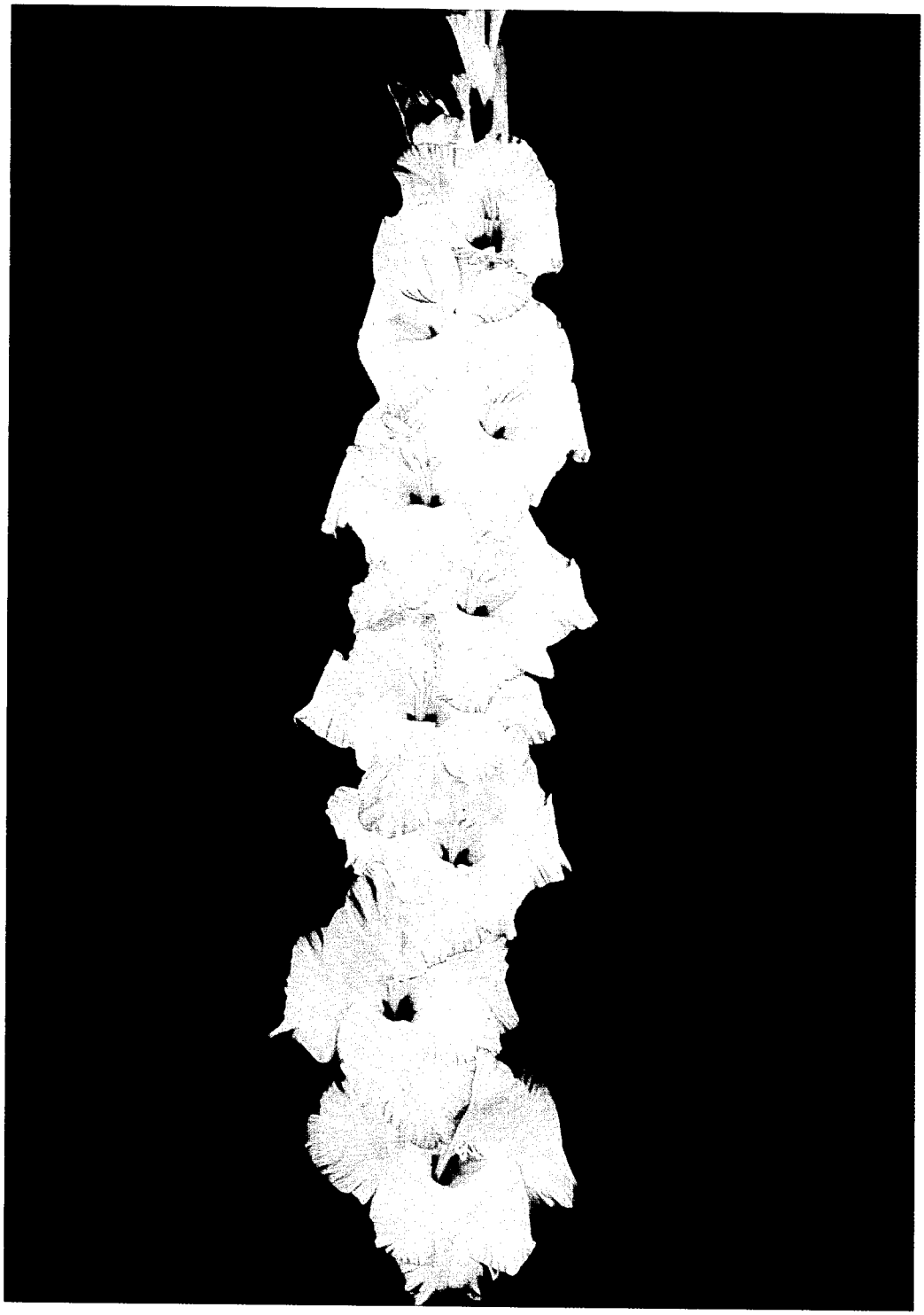

United States Patent Office

Plant Pat. 3,442
Patented Jan. 15, 1974

3,442
GLADIOLUS PLANT

Carl H. Fischer, St. Charles, Minn., assignor to
Selected Glads, Inc., New Albany, Ind.

Filed Nov. 15, 1971, Ser. No. 199,049
Int. Cl. A01h 5/00
U.S. Cl. Plt.—85 1 Claim This invention relates to a new and distinct variety of gladiolus plant.

This new gladiolus plant was originated by me by crossing a seed parent of unknown variety with a pollen parent which was also of unknown origin.

The improved variety resulting from this breeding is evidenced by the following unique combination of characteristics which are outstanding therein and which distinguish my new variety from its parents, as well as from other varieties of which I am aware.

First: A color so unique and distinctive that not other variety resembles mine.

Second: The strong, healthy and robust growth from cormlets.

In addition to these major characteristics my variety is also endowed with the following characteristics:

(1) Good bud count
(2) Stem freedom from crooking
(3) Admirable and consistent growth habits
(4) Excellent propagative powers
(5) Only slight ruffling.

I have asexually reproduced the new variety by cormels through several generations in Minnesota, and succeeding generations have established that the distinguishing characteristics of the variety held true. By natural increase from cormels through several generations its color and other characteristics have proven to be permanently fixed.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction.

The following is a detailed description of our new variety, with color terminology in accordance with the Horticultural Colour Charts issued by the British Colour Council and the Royal Horticultural Society, except where general color terms of ordinary dictionary significance are obvious.

PLANT

Growth: Healthy, vigorous and consistent; excellent propagator.

Blooming habit: Under normal conditions the first bloom appears approximately 85 days after planting in the north central latitudes of the United States, with 6 to 9 florets showing color at one time.

Stems:
*Form.*—Tall and straight.
*Diameter at base.*—About ¾ inch.
*Color at base.*—Purple.

Foliage: Above the ground they are medium green. The average leaf is one and three-quarter inch wide at the base, grows thirty-six inches long, tapers gracefully to a point and droops artistically from the spot where the taper begins, about twenty-four inches from the ground.

Disease resistance: The variety has been found to be unusually resistant to the usual gladiolus plant diseases of a bacterial, viral or fungoid genesis.

Corms: Mature corms are plump and high-crowned with paper-like husks which are straw colored at the point of their attachment, continuing straw colored to near the top.
*Color of flesh.*—Amber yellow—Plate 505/3.

FLOWER

Spike:
*Form and size.*—Tall and straight with bloom spike 60 inches in height and regularly carrying 18 to 20 buds with flowerhead ranging about 24 inches long.

Bud:
*Size.*—About 2 inches long when opening.
*Opening.*—On first blooming 3 or 4 buds open with 2 or 3 a day opening thereafter.

Flower:
*Arrangement.*—Flowerhead of the new variety has an informal placement wherein all florets are not in rows.
*Size.*—Individual florets average about 5 to 5½ inches in diameter.
*Form.*—Florets are slightly round, slightly recurved and only slightly ruffled.
*Keeping qualities.*—The flowers keep well and open exceptionally well from tight buds.

Petals:
*Shape.*—Somewhat round, but flat.
*Size.*—Upper petals—about 2 to 2½ inches wide. Lip pedals—about 1 inch wide.
*Aspect.*—Substance is average. Surface is uneven and slightly ruffled.
*Fragrance.*—None.
*Color.*—Canary yellow—Plate 2 with a ¼ to ½ inch margin of Tyrian Rose—Plate 24/1, the margin at times being somewhat mottled or flecked.

REPRODUCTIVE ORGANS

Stamens:
*Color.*—Purple.

Pistils:
*Color.*—Cream.

GROWTH

Locality where grown and observed.—St. Charles, Minn.

Propagation: Holds its distinguishing characteristics through succeeding propagations from cormels.

It can be seen that this variety is unique in its color, which is an unusual blend of the pink blush of ripe peach into yellow.

What I claim is:

1. A new and distinct variety of gladiolus plant, substantially as herein shown and described, characterized particularly as to novelty by the unique combination of its unique color, which is an unusual blend of the pink blush of ripe peach into yellow, and its strong and healthy growth.

No references cited.

ROBERT E. BAGWILL, Primary Examiner